United States Patent
Ecker

(10) Patent No.: US 6,492,111 B1
(45) Date of Patent: *Dec. 10, 2002

(54) IN SITU BINARY SYNTHESIS OF BIOLOGICALLY EFFECTIVE MOLECULES

(75) Inventor: David J. Ecker, Encinitas, CA (US)

(73) Assignee: Isis Pharmaceuticals, Inc., Carlsbad, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/200,107

(22) Filed: Nov. 25, 1998

(51) Int. Cl.$^7$ ............................ C12Q 1/68; C07H 21/04
(52) U.S. Cl. .................... 435/6; 435/325; 435/91.52; 536/24.3
(58) Field of Search .................... 536/24.3; 435/6, 435/325, 91.52

(56) References Cited

U.S. PATENT DOCUMENTS

| | | |
|---|---|---|
| 5,138,045 A | 8/1992 | Cook et al. .................. 536/27 |
| 5,210,264 A | 5/1993 | Yau ......................... 558/167 |
| 5,212,295 A | 5/1993 | Cook ........................ 536/26.7 |
| 5,214,597 A | 5/1993 | Ito et al. ................ 364/571.01 |
| 5,218,105 A | 6/1993 | Cook et al. ............... 536/25.31 |
| 5,242,906 A | 9/1993 | Pagano et al. ............... 514/44 |
| 5,359,044 A | 10/1994 | Cook et al. ............... 536/23.1 |
| 5,359,051 A | 10/1994 | Cook et al. ............... 536/26.7 |
| 5,378,825 A | 1/1995 | Cook et al. .............. 536/25.34 |
| 5,386,023 A | 1/1995 | Sanghvi et al. ............ 536/25.3 |
| 5,391,667 A | 2/1995 | Dellinger .................... 526/264 |
| 5,424,413 A | 6/1995 | Hogan et al. ............. 536/24.31 |
| 5,451,503 A | * 9/1995 | Hogan et al. .................. 435/6 |
| 5,457,191 A | 10/1995 | Cook et al. .............. 536/27.13 |
| 5,459,255 A | 10/1995 | Cook et al. .............. 536/27.13 |
| 5,487,972 A | * 1/1996 | Gelfand et al. ................. 435/6 |
| 5,489,677 A | 2/1996 | Sanghvi et al. ............ 536/22.1 |
| 5,506,212 A | 4/1996 | Hoke et al. .................. 514/44 |
| 5,506,351 A | 4/1996 | McGee .................... 536/55.3 |
| 5,510,239 A | 4/1996 | Baracchini, Jr. et al. ......... 435/6 |
| 5,510,476 A | 4/1996 | Ravikumar et al. ....... 536/25.31 |
| 5,512,438 A | 4/1996 | Ecker ......................... 435/6 |
| 5,514,786 A | 5/1996 | Cook et al. ............... 536/23.1 |
| 5,514,788 A | 5/1996 | Bennett et al. ............ 536/23.1 |
| 5,519,134 A | 5/1996 | Acevedo et al. ............ 544/243 |
| 5,521,023 A | 5/1996 | Kejha et al. ................ 429/142 |
| 5,523,389 A | 6/1996 | Ecker et al. .............. 536/23.1 |
| 5,539,082 A | 7/1996 | Nielsen et al. .............. 530/300 |
| 5,539,083 A | 7/1996 | Cook et al. ................ 530/333 |
| 5,541,307 A | 7/1996 | Cook et al. ............... 536/23.1 |
| 5,543,507 A | 8/1996 | Cook et al. ............... 536/23.1 |
| 5,554,746 A | 9/1996 | Ravikumar et al. ......... 540/200 |
| 5,563,255 A | 10/1996 | Monia et al. ............. 536/24.31 |
| 5,571,902 A | 11/1996 | Ravikumar et al. ........ 536/22.1 |
| 5,576,208 A | 11/1996 | Monia et al. ............ 435/240.2 |
| 5,576,302 A | 11/1996 | Cook et al. .................. 514/44 |
| 5,578,718 A | 11/1996 | Cook et al. .............. 536/27.21 |
| 5,582,986 A | 12/1996 | Monia et al. .................. 435/6 |
| 5,587,361 A | 12/1996 | Cook et al. .................. 514/44 |
| 5,587,420 A | 12/1996 | Takizawa et al. ........... 524/572 |
| 5,587,469 A | 12/1996 | Cook et al. ............... 536/23.1 |
| 5,595,978 A | 1/1997 | Draper et al. ................ 514/44 |
| 5,599,704 A | 2/1997 | Thompson et al. ......... 435/325 |
| 5,599,706 A | 2/1997 | Stinchcomb et al. ....... 435/366 |
| 5,599,797 A | 2/1997 | Cook et al. .................. 514/44 |
| 5,602,240 A | 2/1997 | De Mesmaeker et al. . 536/23.1 |
| 5,607,923 A | 3/1997 | Cook et al. .................. 514/44 |
| 5,608,046 A | 3/1997 | Cook et al. ............... 536/23.1 |
| 5,610,052 A | 3/1997 | Thompson et al. ......... 435/366 |
| 5,610,289 A | 3/1997 | Cook et al. .............. 536/25.34 |
| 5,614,617 A | 3/1997 | Cook et al. ............... 536/23.1 |
| 5,614,621 A | 3/1997 | Ravikumar et al. ...... 536/25.34 |
| 5,618,704 A | 4/1997 | Sanghvi et al. ............ 435/91.5 |
| 5,620,963 A | 4/1997 | Cook et al. .................. 514/44 |
| 5,623,065 A | 4/1997 | Cook et al. ............... 536/23.1 |
| 5,623,070 A | 4/1997 | Cook et al. ............... 536/27.6 |
| 5,629,152 A | 5/1997 | Ravikumar .................... 435/6 |
| 5,635,385 A | 6/1997 | Leopold et al. ............. 435/325 |
| 5,635,488 A | 6/1997 | Cook et al. .................. 514/44 |
| 5,637,684 A | 6/1997 | Cook et al. ............... 536/23.1 |
| 5,639,655 A | 6/1997 | Thompson et al. ....... 435/240.2 |
| 5,639,873 A | 6/1997 | Barascut et al. ........... 536/25.3 |

(List continued on next page.)

FOREIGN PATENT DOCUMENTS

| | | | | |
|---|---|---|---|---|
| EP | 0 246 864 | * | 11/1987 | ..................... 1/68 |
| WO | WO 93/17128 | * | 9/1993 | ..................... 1/68 |
| WO | WO 95/19449 | * | 7/1995 | ..................... 1/68 |

OTHER PUBLICATIONS

Wittwer et al. "Continuous fluorescence monitoring of Rapid Cycle DNA Amplificiation". BioTechniques, vol. 22, No. 1, 1997, pp. 130–138.*

Sixou et al. "Intracellular oligonucleotide hybridization detected by FRET", Nucleic Acids Research, vol. 22, No. 4, 1994, p. 662–668.*

(List continued on next page.)

*Primary Examiner*—Jeffrey Fredman
*Assistant Examiner*—Jeanine Goldberg
(74) *Attorney, Agent, or Firm*—Woodcock Washburn LLP

(57) ABSTRACT

A plurality of oligonucleotides are caused to bind specifically to target nucleic acid which is predictive of a disease state or a biological condition within cells containing the target nucleic acid. The respective oligonucleotides, which may be functionilized or may be present in the form of oligonucleotide analogs, carry with them a plurality of synthons. Such synthons, which may be identiphores, toxiphores, or other precursors to biologically effective molecules, interact when specific binding of the respective oligonucleotides occurs at sites adjacent to each other on the target nucleic acid. The resulting interaction gives rise to the synthesis, generation or release of highly active biological molecules in situ in the cell in which the specific binding takes place. This permits the use of extraordinarily toxic molecules for use in killing cells containing the target nucleic acids. Imaging and other uses are also provided by the present invention.

9 Claims, No Drawings

U.S. PATENT DOCUMENTS

| | | | |
|---|---|---|---|
| 5,641,486 A | 6/1997 | Hinrichs et al. | 424/139.1 |
| 5,641,625 A | 6/1997 | Ecker et al. | 435/6 |
| 5,643,780 A | 7/1997 | Baker | 435/375 |
| 5,644,048 A | 7/1997 | Yau | 536/25.3 |
| 5,646,265 A | 7/1997 | McGee | 536/25.34 |
| 5,654,284 A | 8/1997 | Cook et al. | 514/44 |
| 5,656,612 A | 8/1997 | Monia | 514/44 |
| 5,656,743 A | 8/1997 | Busch et al. | 536/24.5 |
| 5,658,891 A | 8/1997 | Draper et al. | 514/44 |
| 5,661,134 A | 8/1997 | Cook et al. | 514/44 |
| 5,668,165 A | 9/1997 | Wuonola et al. | 514/397 |
| 5,670,633 A | 9/1997 | Cook et al. | 536/23.1 |
| 5,677,437 A | 10/1997 | Teng et al. | 536/23.1 |
| 5,681,941 A | 10/1997 | Cook et al. | 536/23.1 |
| 5,681,943 A * | 10/1997 | Letsinger et al. | 536/25.33 |
| 5,681,944 A | 10/1997 | Crooke et al. | 536/24.5 |
| 5,683,873 A | 11/1997 | George et al. | 435/6 |
| 5,688,941 A | 11/1997 | Cook et al. | 536/25.3 |
| 5,691,461 A | 11/1997 | Ecker et al. | 536/24.32 |
| 5,700,922 A | 12/1997 | Cook | 536/23.1 |
| 5,703,054 A | 12/1997 | Bennett et al. | 514/44 |
| 5,714,331 A | 2/1998 | Buchardt et al. | 435/6 |
| 5,714,606 A | 2/1998 | Acevedo et al. | 544/243 |
| 5,717,083 A | 2/1998 | Cook et al. | 536/23.1 |
| 5,719,262 A | 2/1998 | Buchardt et al. | 530/300 |
| 5,719,271 A | 2/1998 | Cook et al. | 536/23.1 |
| 5,731,438 A | 3/1998 | Cook et al. | 544/368 |
| 5,734,041 A | 3/1998 | Just et al. | 536/25.31 |
| 5,736,294 A | 4/1998 | Ecker et al. | 435/240.2 |
| 5,736,336 A | 4/1998 | Buchardt et al. | 435/6 |
| 5,744,361 A | 4/1998 | Hoffman et al. | 435/372 |
| 5,747,335 A | 5/1998 | Haseloff et al. | 435/325 |
| 5,750,692 A | 5/1998 | Cook et al. | 544/253 |
| 5,756,282 A | 5/1998 | Crooke et al. | 435/5 |
| 5,760,202 A | 6/1998 | Cook et al. | 536/22.1 |
| 5,766,855 A | 6/1998 | Buchardt et al. | 435/6 |
| 5,766,942 A | 6/1998 | Haseloff et al. | 435/325 |
| 5,770,713 A | 6/1998 | Imbach et al. | 536/22.1 |
| 5,773,571 A | 6/1998 | Nielsen et al. | 530/300 |
| 5,783,682 A | 7/1998 | Cook et al. | 536/24.3 |
| 5,786,461 A | 7/1998 | Buchardt et al. | 536/18.7 |
| 5,792,844 A | 8/1998 | Sanghvi et al. | 536/23.1 |
| 5,798,360 A | 8/1998 | Cook et al. | 514/255 |
| 5,801,158 A | 9/1998 | Thompson et al. | 514/44 |
| 5,808,023 A | 9/1998 | Sanghvi et al. | 536/23.1 |
| 5,808,027 A | 9/1998 | Cook et al. | 536/23.1 |
| 5,811,534 A | 9/1998 | Cook et al. | 536/23.1 |
| 5,814,629 A | 9/1998 | Stanetty et al. | 514/234.2 |
| 5,817,489 A | 10/1998 | Cook et al. | 435/117 |
| 5,831,014 A | 11/1998 | Cook et al. | 530/350 |
| 5,834,185 A | 11/1998 | Ts'o et al. | 435/6 |
| 5,834,607 A | 11/1998 | Manoharan et al. | 536/22.1 |
| 5,874,555 A | 2/1999 | Dervan et al. | 536/23.1 |
| 5,939,256 A * | 8/1999 | Yamamoto et al. | 435/6 |

OTHER PUBLICATIONS

Sacchi et al. "Interphase Cytognetics of the t(8;21)(q22;q22) Associated with Acute myelogenous leukemia by two–color FISH" Cancer Genetic Cytogenetics, vol. 79, 1995, p. 97–103.*

Viassov et al., "Binary Systems of Oligonucleotide Conjugates for Sequence Specific Energy—Transfer Sensitized Photomodification of Nucleic Acids," NATO ASI Ser., Ser. C, 479, DNA and RNA Cleavers and Chemotherapy of Cancer and Viral Diseases, 1996, 195–207.

Viassov et al., "Sequence Specific Cleavage of Yeast tRNA–Phe with Oligonucelotides Conjugated to Diimidazole Construction", *Antisense Nucleic Drug Development*, 1997, 7(1), 39–42.

Yurchenko et al, "Cleavage of Leishmania Mini—Exon Sequence by Oligonucleotides Conjugated to a Diimidazole Construction," *Nucleosides and Nucleosides*, 1996, 16(7–9), 1721–1725.

U.S. patent application Ser. No. 09/076,404, Ecker et al., filed May 12, 1998.

U.S. patent application Ser No. 09/076,440, Ecker et al., filed May 12, 1998.

U.S. patent application Ser. No. 09/076,447, Griffey et al., filed May 12, 1998.

Choe, S. et al., "The crystal structure of diphtheria toxin," *Nature*, 1992, 357, 216–222.

DeWolf, M.J.S. et al., "Regeneration of active receptor recognition domains on the B subunit of cholera toxin by formation of hybrids from chemically inactivated derivatives," *Biochim. et Biophy. Acta*, 1994, 1223, 285–295.

Wahlsten, J.L. et al., "Separation of Function Between the Domains of Toxic Shock Syndrome Toxin–1," *J. Immunol.*, 1998, 13(2), 854–859.

Williams, M.D. et al., "Production of Recombinant $Dt_{ct}$G-MCSF Fusion Toxin in a Baculovirus Expression Vector System for Biotherapy of GMCSF–Receptor Positive Hematologic Malignancies," *Protein Expression Purification*, 1998, 13, 210–221.

* cited by examiner

IN SITU BINARY SYNTHESIS OF BIOLOGICALLY EFFECTIVE MOLECULES

FIELD OF THE INVENTION

The present invention is directed to the synthesis, generation or release of molecules within cells and tissues, which molecules have significant, biological effects. Such molecules are synthesized which permit the identification of the cells or tissues, which destroy the cells or tissues, which moderate, modulate, or enhance cellular or tissue function, or which otherwise have a diagnostic, therapeutic, nutritional or other biological effect.

The in situ generation of such molecules is specific to particular cells and tissues such that the molecules thus formed or released are delivered specifically to the cells or tissues in question. Such high specificity of delivery overcomes many therapeutic impediments and can provide high "leverage" with concomitant low side effects.

BACKGROUND OF THE INVENTION

It has long been known to employ nucleic acid structures present in cells to serve as "targets" for diagnostic and therapeutic regimes. A classical example of such employment is evidenced by the field of antisense therapeutics. According to the antisense paradigm, a nucleic acid sequence or structure is identified as being associated with the production of a gene product—usually a peptide—which has deleterious effects upon cells or tissues. The target nucleic acid may be an oncogene, an mRNA associated with the genesis or development of a disease state or a hyperproliferative gene structures which proliferation is to be reduced or eliminated.

Under the antisense paradigm, oligonucleotides are designed which are specifically bindable to a nucleic acids sequence or structure, usually mRNA, the down regulation of which is desired. The oligonucleotide, usually in the form of a chemically modified analog or construct, is administered to the cells containing the targeted nucleic acid. The specific binding of the oligonucleotide interferes with expression of the mRNA, thus interfering with its function and expression. Protein normally expressed by the mRNA is either not expressed at all or is expressed in much lower quantity with a concomitant, beneficial therapeutic effect. The paradigm may also be used for diagnosis and research in ways which are well known to persons of ordinary skill in the art.

The antisense paradigm is well understood per se to persons of ordinary skill in the art and there are numerous review articles which describe in detail varying approaches to this practice.

Nucleic acids which can be used to target in accordance with some embodiments of this invention include mRNA molecules, which preferably have secondary structures such as stem-loop structures, or unique secondary structural sites, a such as the molecular interaction sites taught in U.S. application Ser. Nos. 09/076,440, 09/076,447, and 09/076,404, each of which is incorporated herein by reference in its entirety.

Potential target nucleic acids include, but are not limited to, mammalian, bacterial, fungal and viral mRNA. Oligonucleotides have been shown to bind to numerous targets including, for example, Candida (U.S. Pat. No. 5,691,461), protein kinase C (U.S. Pat. Nos. 5,703,054, 5,681,944, and 5,620,963), papillomavirus (U.S. Pat. Nos. 5,681,944 and 5,756,282), herpesvirus (U.S. Pat. No. 5,658,891), cytomegalovirus (U.S. Pat. Nos. 5,607,923 and 5,595,978), human immunodeficiency virus (U.S. Pat. No. 5,523,389), ras (U.S. Pat. Nos. 5,661,134, 5,582,986, and 5,576,208), Epstein-Barr virus (U.S. Pat. No. 5,242,906), cell adhesion molecules (U.S. Pat. Nos. 5,599,797 and 5,514,788), hepatitis virus (U.S. Pat. No. 5,576,302), Raf kinase (U.S. Pat. Nos. 5,654,284, 5,563,255, 5,656,612, and 5,744,361), p120 (U.S. Pat. No. 5,814,629), cell growth (U.S. Pat. No. 5,656,743), and multi-drug resistance associated protein (U.S. Pat. No. 5,510,239). Each of the above-identified patents is incorporated herein by reference in its entirety.

In addition to traditional antisense mechanisms, oligonucleotides have also been shown to act through mechanisms, for example, involving pseudo-half-knot formulations (U.S. Pat. No. 5,512,438), 5'-cap inhibition (U.S. Pat. No. 5,643,780), and triple helix formation (U.S. Pat. No. 5,834,185), each of which is incorporated herein by reference in its entirety. All such targets and many more may be used herein.

It has also been proposed to employ a pair of oligonucleotides to bind specifically with a mRNA in an antisense fashion. (see Viassov et al., "*Binary Systems of Oligonucleotide Conjugates for Sequence Specific Energy—Transfer Sensitized Photomodification of Nucleic Acids*" NATO ASI Ser., Ser. C, 479 (DNA and RNA Cleavers and Chemotherapy of Cancer and Viral Diseases) 195–207, (1996). Viassov discloses that, along with one oligonucleotide there is a flourescent sensitizer, while the other oligonucleotide carries a structure which, when irradiated with ultraviolet radiation, is known to react with nucleic acids. Viassov demonstrates a rapid modification of the DNA to which the oligonucleotides were targeted when the two oligonucleotides are allowed to bind to adjacent sites on the DNA and be subsequently irradiated. The proximity of the photosensitizer to the group which transfers energy to the DNA was viewed to be important to the reaction with the DNA.

The technique of fluorescence resonance energy transfer (FRET) has been used, inter alia to identify point mutations in nucleic acids. A pair of oligonucleotides, each of which carries a fluorophores are caused to bind to nucleic acids. Through study of their fluorescence behavior, determination of the proximity of the fluorophores and, hence, the presence or absence of intervening base units, can give rise to the desired mutational information. FRET can also monitor ribozyme interactions and seems to be useful generally in nucleic acid research.

Viassov et al in, "*Sequence Specific Cleavage of Yeast tRNA-Phe with Oligonucelotides Conjugated to Diimidazole Construction*", Antisense Nucleic Drug Development, 7(1): 39–42, (1997), prepares oligonucleotides conjugated to a chemical construction having two histidine residues. Yurchenko et al, "*Cleavage of Leishmania Mini—Exon Sequence by Oligonucleotides Conjugated to a Diimidazole Construction*", Nucleosides and Nucleosides, 16 (7–9): 1721–1725, (1996), is directed to similar subject matter. While it has been known to conjugate a plurality of oligonucleotides to a single nucleic acid in a sequence specific fashion, all such techniques are believe to have been directed to the incapacitation or destruction of the nucleic acid target. While this can certainly have some useful applications, it is limited in its applicability.

It has been greatly desired to provide for the targeting of nucleic acids in a way different from the traditional, antisense approach. Thus, improvements over antisense methodology and over the methodologies for nucleic acid cleavage of, e.g. Viassov and Yurchenko are greatly desired. In particular, a methodology that does not necessarily involve the incapacitation of the target nucleic acid but which has a vastly more significant therapeutic potential have long been desired. The present invention is directed to this new paradigm of therapeutics and diagnostics.

SUMMARY OF THE INVENTION

The present invention provides a dramatic divergence in oligonucleotide therapeutics, diagnostics and related paradigms. In accordance with the invention, a nucleic acid target which has been identified as being present in the cell or tissue of interest is caused to be the object of specific binding by a plurality of oligonucleotides. By virtue of the specific binding of the two or more oligonucleotides, which binding is caused to take place at adjacent sites on the target nucleic acid, a molecular species is either synthesized, formed or released. The molecular species has great biological effect within the cell or tissue which, of course, carries the target nucleic acid. By virtue of the formation, synthesis or release of such biologically effective molecules, cells having the target nucleic acid may either be identified, imaged, killed, benefitted or modified in some significant way. Overall, this paradigm is denominated "in situ binary synthesis," since a molecule having biological activity is created upon the specific binding of oligonucleotides to the target nucleic acid. The method is in situ since the formation, synthesis or release of the molecule takes place in situ—within the cell or tissue.

It is apparent that the generation of these biologically active molecules, occurring as it does within the cell or tissue which has been targeted, is extraordinarily specific. Moreover, the generation of only a few molecules in this way can have an extraordinary and profound effect upon the cells or tissues. Thus, the molecules to be synthesized, generated or released are not spread out over an entire organism, but, rather, only within the cells or tissues which have been targeted. Extraordinary "leverage" can thus be obtained, such that a very small total amount of biologically active material need be formed in order to obtain a very large biological effect. Side effects are concomitantly diminished. Indeed, molecules may be selected in this way for generation, synthesis or release which could never be considered for diagnostic or therapeutic use under any other paradigm. As will be seen, even extraordinarily toxic molecules can find use in therapeutics so long as they are confined through the use of the present methodology to the particular cellular locus where they are needed.

The methodologies of the present invention do not necessarily involve modification of nucleic acid, or at least not the nucleic acid which serves as a targeting nucleic acid. Thus, unlike prior oligonucleotide diagnostic and therapeutic regimes, the objective of a specific binding of an oligonucleotide is not necessarily destruction or inhibition of the nucleic acid, usually mRNA, which has been targeted. Rather, the nucleic acid simply serves as the "locator beacon" and as a place for the docking of oligonucleotides by virtue of their specific binding. As will be seen, the ability of a plurality of oligonucleotides to specifically bind to a target nucleic acid at adjacent sites upon the nucleic acid permits the generation, synthesis or release of the biologically effective molecules in a very highly controlled fashion. Thus, wherever such specific binding at adjacent sites does not occur, generation, synthesis or release of the biological molecule does not take place. This high degree of control contributes to the utility of the present invention in that extraordinary toxic or potent molecules may be used without the worry of accidental generation or release of such molecules at locations other than the ones desired.

The present invention, to some extent, builds upon previous methodologies of oligonucleotide interaction with cellular nucleic acids, especially mRNA in the following way. It is well known to identify nucleic acids structures or sequences which are related to disease states. It is also known how to prepare oligonucleotides which have antisense sequences to the nucleic acids whose function or activity is to be moderated or ended. Moreover, a wide variety of chemical modifications of nucleic acids, and, indeed, a host of oligonucleotide analogs are known for this purpose. It is similarly well understood how to contact cells or tissues with an oligonucleotide or oligonucleotide analog in such a way as to cause formation of a heteroduplex between the oligonucleotide and the target nucleic acid. Such heteroduplex formation traditionally leads to the destruction of the nucleic acid or to a failure in its translation into protein. A number of intermediate results may attend this interaction. Thus, the binding of the oligonucleotide may activate RNAse H to cleave the nucleic acid. Alternatively, specific binding may simply make it impossible for the nucleic acid to be translated into protein. A number of other methodologies have been proposed for oligonucleotide interaction with nucleic acids, however these are generally attended by interference with the structure or activity of the target nucleic acid.

It follows from the foregoing that it is essential that the target nucleic acid be one which is important to disease states. It is not enough, under these prime paradigms, for the nucleic acid merely to be associated with a cell or tissue which is in a disease state. It may be immediately seen that interaction with a non-critical nucleic acid, such as an mRNA, even if very specific and entirely efficacious, will not lead to any beneficial results since the expression of the mRNA is not vital to survival of the cell or tissue. Moreover, antisense interaction with nucleic acids, while much more efficient than small molecule interaction with peptides, still requires the individual, specific binding of oligonucleotide to individual nucleic acids, such as mRNAs.

Contrarily, the present invention does not require the identification of a target nucleic acid which is vital to the function of a cell on which is causative of a disease state. Indeed the nucleic acid thus identified need not actually be translated into protein in large quantities within the cell or tissue in question. Rather, it is only necessary that the target nucleic acid be associated with or predictive of the existence of the disease state or other state of interest in cells or tissues to be treated. This is so because it is not the inactivation of the nucleic acid which is sought, but rather the use of that nucleic acid to target oligonucleotides to the cells or tissues which contain the target nucleic acid.

In accordance with preferred embodiments of this invention, a plurality of oligonucleotides are formulated to be specifically bindable to the target nucleic acid. Moreover, such oligonucleotides are formulated to have sequences which cause them to specifically bind to the target nucleic acid at adjacent sites. While it is possible that the oligonucleotides could bind at sites which are removed by one or two bases, it is greatly preferred that the oligonucleotides bind immediately adjacent to each other. It will, thus, be seen that the present methodology causes two oligonucleotides to enter a cell, tissue, or preparation having target nucleic acid and to bind to the target nucleic acid "right next to" each other. This close, predicable, and regulatable proximity of oligonucleotides to each other that contributes to the present invention.

Reliable and precise, specific binding of two designed oligonucleotides to each other within a cell containing a preselected, target nucleic acid permits the specific synthesis, formulation or release of a molecular species when—but only when—such specific binding occurs. Thus, a first one of the oligonucleotides carries with it a first portion of the biologically effective molecule to be synthesized, formulated or released. The second oligonucleotide carries with it a second portion of the biologically effective molecule. It is only when the first and second portions of the molecules are brought together in physical proximity and, preferably, with careful geometric alignment, that the biological molecule is either synthesized, generated, or released. It is also possible to have an essentially complete biologically effective molecule from part of one of the oligonucleotides with a moiety on the second oligonucleotide being capable of either altering, transforming, cleaving, or releasing the first biologically effective molecule or molecule precursor. In any event, whether the biologically effective molecule is actually synthesized through the joining together with covalent bonds of two or more fragments or synthons thereof, whether a precursor molecule is transformed, modified, or cleaved during this process, or whether a pre-formed, biologically effective molecule is cleaved or released from the oligonucleotides through the present methodology, the biologically effected molecule is not rendered effective unless and until the two oligonucleotides specifically bind at adjacent sites on the target nucleic acid within the cell, tissue, or in vitro preparation.

It will be seen that the first oligonucleotide carries with it a first synthon while the second oligonucleotide carries with or on it, or otherwise comprises, a second synthon. Persons of ordinary skill in the art will understand that the term "synthon" is extraordinarily broad and means a chemical moiety which is capable of interacting with another chemical moiety to give rise to chemical alteration.

While the invention is amenable to the use of a pair of oligonucleotides for interaction with the target nucleic acid, other paradigms are also possible within the spirit of the invention. Thus, an oligonucleotide may specifically bind to the target nucleic acid followed by the interaction of the heteroduplex with another species, which is not an oligonucleotide. Such other species may be, for example, a peptide, a carbohydrate or complex sugar, or a "small" molecule, e.g. a non-oligomer. The confluence of two or more molecules in some specific relationship with target nucleic acid followed by the synthesis, generation or release of a molecular species having significant biological effect, especially toxic effect.

Certain aspects of the invention provide for the employment of two or more non-oligonucleotides in the practice hereof. Thus, specific binding of two or more non-oligonucleotide oligomers, carbohydrates or sugars, or small molecules may serve the purposes described herein. Thus, two or more small molecules could bind specifically and adjacently to the target nucleic acid, giving rise to a biologically active molecular species for, e.g. destruction of the cell containing the target nucleic acid or detection thereof.

The present invention provides for the detection of cells or nucleic acids found in the cells, with the killing of cells having target nucleic acids, and with certain other beneficial results. While, in all such cases, it may be seen that the respective oligonucleotides carry with them synthons, in accordance with the broad definition of that term, it may also be convenient to refer to the chemical moieties carried by the respective oligonucleotides in terms which are more nearly suited to their function. Thus, when it is desired to achieve the identification of cells or tissues containing target nucleic acid, the respective synthons carried by the oligonucleotides may be referred to as "identiphores." In this context, the identiphores are moieties which can interact with each other to give rise to either an interaction or a molecular species which can be detected in some way.

Detection may take place using any form of spectroscopy, x-ray examination, biochemical or biological analyses or otherwise. What is required is that the confluence of the two identiphores carried, respectively, by the oligonucleotides which specifically bind to the target nucleic acid, be detectable. The presence of the detectable moiety formed, synthesized or released by the conjunction in space of the two identiphores is, according to this embodiment, probative of the presence of the target nucleic acid in the cell, tissue or in vitro assay.

As persons of skill in the art will appreciate, x-ray detection may be employed. This is particularly beneficial when the identiphore contains a heavy metal such as a heavy metal contained within an heterocyclic structure such as a porphyrin, heme or similar species. The identiphores may form a charged transfer complex when in proximity with each other which complex may be detectable through spectroscopy. Such identiphores may also become covalently bonded with each other upon coming into proximity giving rise to a chemical moiety or molecule which can, itself be detected. Other forms of detection including magnetic resonance spectroscopy, proton magnetic resonance spectroscopy, electron resonance spectroscopy, fluorescence spectroscopy or electromagnetic spectroscopy may also be profitable employed in connection with this embodiment of the invention.

For example, the identiphores can comprise portions of a charge transfer complex of TTF-TCNQ, (Tetrathiafulvalene and Tetracyanoquinodimethane). Alternately, Bis-(ethylenedithio)dithiapyrene (ETDTYP) and Dibenzo barreleno tetracyano quino dimethane or Triphenylphosphine and Acrylonitrile could form such complexes. Other charge transfer complexes are known to persons of ordinary skill in the art. Thus, these molecular moieties may be caused to comprise the oligonucleotides which specifically bind to the target nucleic acid. Bringing the two identiphores into proximity gives rise to the detectable complex.

The use of identiphores for identifying the presence of target nucleic acid in cells or tissues may be used to diagnose certain cellular biological states such as disease states, especially hyperproliferative states and cancers.

As with most aspects of the present invention, the identiphores are best placed into spacial proximity with each other and also to have a preselected geometric relationship one to the other. This is especially true when intermolecular interactions are required such as charge transfer complexes and the like.

This aspect of the invention provides methods for identifying cells containing a preselected nucleic acid sequence. These methods comprise contacting the cells with a first oligonucleotide specifically bindable with the preselected nucleic acid, the first oligonucleotide comprising a first identiphore. The cells are also contacted with the second oligonucleotide specifically bindable with the preselected nucleic acid, preferably at a site immediately adjacent to the site where the first oligonucleotide has bound to the nucleic acid. The second oligonucleotide also comprises an identiphore. The first and second identiphores are detectable when in proximity with each other. Thus, they may either react with each other to form a new molecular species, cause a species to be released from the oligonucleotides for detection, or may give rise to an entirely new moiety which, itself, may be detected in any of the ways known to persons of ordinary skill in the art.

In accordance with other preferred embodiments of the present invention, the synthons carried by the respective oligonucleotides may give rise to toxic molecules. Such molecules may either be synthesized, generated or released upon the specific binding of the two oligonucleotides to adjacent sites on the target nucleic acid. The generation of a toxic molecule as a result of this specific binding gives rise to cell death and possibly even destruction of tissue material in adjacent cells. It will be appreciated that many highly toxic molecules exist in nature and otherwise which can effectuate widespread destruction on a cellular and tissue level. Prior therapeutic regimes have never been able to exploit this phenomenon, since systemic or untargeted toxicity has never been able to be avoided heretofore. The present invention, however, permits this.

Thus, the present invention provides methods of killing cells, which cells contain a preselected nucleic acid. The method comprises contacting the cells with a first oligonucleotide specifically bindable with the selected preselected nucleic acid. The first oligonucleotide comprises a first toxiphore. It would be understood that the term "toxiphore" is meant herein to mean a chemical species which, when combined with one or more additional toxiphores, gives rise to a toxic molecular species, interaction or phenomenon. Such toxicity is to be expressed on a cellular or tissue level; it is not necessary that any particular nucleic acid be inactivated or "killed" thereby. The method further comprises contacting these preselected nucleic acid sequence with a second oligonucleotide specifically bindable with it. The second oligonucleotide contains a second toxiphore. The first and second toxiphores either synthesize, generate or release a toxin upon coming into proximity with each other as is the case when the two oligonucleotides, carrying their toxiphores, specifically bind to adjacent sites on the target nucleic acid.

It is, of course, preferred that the toxiphores be placed into spatial proximity when the oligonucleotides specifically bind to the target nucleic acids. Additionally, it is greatly preferred that the toxiphores be oriented geometrically so as to facilitate the formation of the molecular species, its generation or release.

In accordance with preferred embodiments, the toxiphores become chemically bonded one to the other to give rise to the toxic, molecular specie. Such specie is, of course, highly biologically effective. It is also within the spirit of this invention that one toxiphore modify the second toxiphore to give rise to the biologically effective, toxic molecule. One toxiphore may also cleave from the oligonucleotide, the heteroduplex, or otherwise, a toxic species.

As will be appreciated, it is desired that the preselected nucleic acid, to which the oligonucleotides and their related toxiphores will specifically attach, be predictive of a cellular biological state. Such state is usually a disease state, especially a hyperproliferative state or one indicative of cancer. Other cellular or tissues states may also be associated with the preselected nucleic acid and, indeed, the present invention may be used in the sense of a probe as well as in the sense of a therapeutic or diagnostic. A host of research functions may also be benefitted through use of the present invention.

The toxic molecule which, in accordance with preferred embodiments of this invention, are synthesized, generated or released may be anything which has effective, preferably powerful cellular toxicity within related tissues or organs. For example, the toxin may be a peptide such as ricin, sarcin, or diphtheria, botulism, etc. toxins. In such cases, the toxin would comprise a functional domain of the toxin. The toxin may be bacterial. The toxin need not be a peptide. For example, the toxin could be an amphibian toxin such as tetradotoxin or bufotoxin. The toxins may also be from invertebrates, such as arachnids, or from reptiles or amphibians. In short, any number of toxins may be employed in conjunction with the present invention. It is preferred that the toxin be very powerful such that only a few, perhaps as few as one or two molecules of the toxin are necessary to effect cell death. Numbers of toxin molecules fewer than ten are preferred in accordance with certain embodiments to kill any given cell. As will be appreciated, a preferred embodiment of the present aspect of the invention is for the treatment of disease state in mammals. Thus, a tissue of a mammal is contacted with the oligonucleotides having toxiphores associated therewith under conditions such that heteroduplexes can be formed. Alternately, in vitro embodiments, heteroduplex formation is encouraged through appropriate selection of reaction conditions. Upon the specific binding of the oligonucleotides to the preselected nucleic acid, the toxiphores interact with each other to give rise to a toxic molecule or other toxic effect.

When the toxin is a peptide, it can be sufficient that a carboxylic acid "end" of a toxiphore be brought into spatial proximity with an amine "end" of another toxiphore, and the same be carefully oriented in space and with geometric precision. In such case, the activation energy required for the formation of the peptide bond may be significantly lowered such that spontaneous generation of the peptide bond occurs. The resulting, toxin is then either active immediately or can be released or cleaved from the complex for toxic activity. Organic molecules other than peptides may also be prepared in this way, cleaved, modified, or released.

The chemical species which effects the toxic activity may also be other than an organic species; they may be organometallic or even inorganic. Thus, one toxiphore might contain a complex metal ion which, in uncomplexed form or in a different oxidation state is highly toxic. The interaction with the second toxiphore may give rise to the toxic form of the metal ion or to its complex. A number of "heavy" metallic species and some which are not so "heavy" are known to be highly toxic in one or another form. All of these are contemplated by the present invention.

As is apparent, the present invention provides for the in situ synthesis of chemical species. This is accomplished through specifically binding first and second oligonucleotides to a preselected nucleic acid at adjacent sites of the nucleic acid. First and second sythons, related to or forming part of the respective oligonucleotides, are then reacted with each other or caused to interact to give rise to a new molecular species or an altered form of an existing molecular species. Significant biological effects may thus be generated upon the cell or tissues comprising those cells.

As will be apparent, a wide variety of organic, organometallic and other inorganic molecules can be formed through the practice of the present invention. As discussed herein above, peptides may be prepared by bringing together two synthons comprising peptide residues, which residues, when carefully oriented in space and oriented as to geometry may form the peptide bond either spontaneously or through the intervention of a catalyst. Indeed, a catalytic agent may also be included in one or more of the oligonucleotides. A host of other organic molecules may similarly be formed as will be apparent to persons of ordinary skill in the art. Organometallic materials may also be prepared hereby and the oxidation state of organic, and organometallic species may be changed through intermediation of oxidizing and reducing agents forming part or all of one or both of the synthons. The charged transfer complexes as discussed herein before may also be placed into apposition and may be used in either a catalytic, synthetic, biologically active or other functional applications. As is apparent, the ability of the present invention to orient synthons in precise proximity and in exact geometric relationship one with the other permits the overcoming of activation energies which would otherwise apply. Accordingly, even reactions which seem extraordinarily slow under solution conditions, may run at sensible rates when synthesized in accordance with the present invention.

It is also within the spirit of the present invention to alter, cleave, release or otherwise furnish chemical moieties through the interaction with the plurality of synthons placed into proximity in this way. Thus, active chemical species may be cleaved from the parent oligonucleotides and from the heteroduplexes to which they have been attracted through the action of the other synthon or otherwise.

Accordingly, the present invention provides for the preparation of such chemical species in amounts which are detectable in cells containing the target nucleic acid. It is, of course, preferred that such nucleic acid be predictive of a biological condition or disease state such that the preparation and delivery of the molecules thus formed or furnished is delivered in situ to such cells. Diagnosis, therapy, or killing of the cell may ensue.

The present invention also provides compositions of matter. In accordance with one embodiment, the invention provides a pair of oligonucleotides each of which is specifically bindable with a preselected nucleic acid. The binding of the pair of oligonucleotides is preferably at adjacent sites on the preselected nucleic acid. Each of the oligonucleotides comprises a portion of a molecular species, which species is formed when the adjacent, specific binding of the oligonucleotides to the nucleic acid occurs. Any of the foregoing methodologies may give rise to pairs of oligonucleotides which are contemplated by the present invention. Indeed, the present invention may also be applied to additional oligonucleotides with additional synthons (toxiphores, identiphores, etc.) whereupon binding of three or more oligonucleotides to adjacent sites on the target nucleic acid is accomplished with results analogous to those described herein above. As will be appreciated, the oligonucleotides may give rise to toxins, charge transfer complexes, detectable molecules for detection and sensing, cell regulatory moieties, nutritional species, and to a wide variety of other compounds having biological activity. The present invention is also directed to compositions of matter comprising a pair of oligonucleotides as herein above together with a diluent or carrier, especially a pharmaceutically acceptable diluent or carrier.

In the present description of the invention, the term oligonucleotide has been used very broadly. Persons of ordinary skill in art will appreciate that the term includes wild type oligonucleotides, those which are unmodified in any way in terms of their chemical construction or substituents. The term also includes semisynthetic and modified oligonucleotides and molecules which are analogous to oligonucleotides. In this context, oligonucleotide includes peptide nucleic acids, "PNAs", molecules which are analogous in function and spatial relationships to nucleic acids and which may be used in oligonucleotide therapeutics such as antisense and the like. These have been well-characterized in the literature and are set forth in number of U.S. patents, many of which are assigned to the assignee of the present application. Each of these are incorporated herein by reference.

Thus, numerous other identophores have been shown to bind mRNA including, for example, peptide nucleic acids (U.S. Pat. Nos. 5,641,625, 5,700,922, 5,719,262, 5,714,331, 5,766,855, 5,773,571, 5,786,461, and 5,736,336, each of which is incorporated herein by reference in its entirety), ribozymes (U.S. Pat. Nos. 5,599,706, 5,801,158, 5,639,655, 5,635,385, 5,599,704, 5,610,052, 5,766,942, and 5,747,335, each of which is incorporated herein by reference in its entirety), and small molecules (U.S. Pat. Nos. 5,668,165, 5,641,486, and 5,683,873, each of which is incorporated herein by reference in its entirety).

Chemically modified oligonucleotides include those which are modified in the backbone, e.g. phosphorothioate, methylphosphonates and a host of other backbone modifications as well as modifications to the substituents on the sugar rings present in the oligomers. Further modifications may be had on the base structure in a number of ways. These are exemplified by a number of U.S. patents including many owned by the assignee of the present application. Each of these in incorporated in full by reference in order to provide more explanation of the full scope of the oligonucleotides which may be employed in connection with the present invention: U.S. Pat. Nos. 5,618,704, 5,608,046, 5,792,844, 5,808,023, 5,834,607, 5,138,045, 5,378,825, 5,359,051, 5,212,295, 5,736,294, 5,614,617, 5,670,633, 5,681,941, 5,359,044, 5,210,264, 5,218,105, 5,610,289, 5,506,351, 5,391,667, 5,514,786, 5,489,677, 5,541,307, 5,386,023, 5,457,191, 5,578,718, 5,644,048, 5,623,065, 5,719,271, 5,637,684, 5,783,682, 5,539,082, 5,614,621, 5,459,255, 5,521,023, 5,539,083, 5,510,476, 5,629,152, 5,554,746, 5,571,902, 5,519,134, 5,543,507, 5,734,041, 5,506,212, 5,714,606, 5,717,083, 5,831,014, 5,677,437, 5,623,070, 5,688,941, 5,808,027, 5,750,692, 5,639,873, 5,731,438, 5,798,360, 5,646,265, 5,760,202, 5,587,361, 5,635,488, 5,587,469, 5,587,420, 5,770,713, 5,214,597, 5,817,489, 5,811,534 and 5,602,240.

While the present invention has been exemplified in terms of the use of a plurality of oligonucleotides to bind specifically to target nucleic acid and to effect the synthesis, generation or release of biologically useful molecules thereby, certain other materials may also be employed. Thus, it may be seen that a first oligonucleotide carrying a synthon (identiphore, toxiphore, etc.) may be caused to bind specifically to a site of a target nucleic acid. Another biooligomer may then be caused to bind to the heteroduplex thus formed. This latter oligomer need not necessarily be an oligonucleotide. Thus, certain peptides are known to be able to complex with heteroduplexes formed between a nucleic acids and oligonucleotides. It is possible to include a synthon along with such peptide and to cause the same to bind the heteroduplex thus bringing the synthon of the peptide and the synthon carried by the oligonucleotide into proximity with the results explained above. Many other variations are possible in accordance with the full spirit of the present invention.

It is also believed to be possible to use a single oligonucleotide to accomplish the function presently exemplified through a plurality of oligonucleotides. Thus, a single oligonucleotide having two portions, each of the two portions carrying a synthon (identiphore, toxiphore, etc.) may be employed. If the two portions of the single oligonucleotide can bind at adjacent locations on the target nucleic acid, thus bringing the synthons into proximity, the spirit of the present invention may be accomplished. It may also be that a single oligomer which first binds with the target nucleic acid and then binds with the heterodymer formed by the first part of the oligomer and the target nucleic acid could be used in conjunction with certain embodiments of the present invention.

While the present invention has been exemplified with respect to certain of its preferred embodiments in considerable detail, persons of ordinary skill will know that other embodiments remain within the scope of the true spirit of the invention.

What is claimed is:

1. A method for identifying cells containing a preselected nucleic acid sequence comprising:

contacting said cells with a first oligonucleotide specifically bindable with said preselected nucleic acid sequence, said first oligonucleotide comprising a first identiphore;

contacting said cells with a second oligonucleotide comprising a second identiphore, wherein said second oligonucleotide is specifically bindable with said preselected nucleic acid sequence at a site adjacent to said first oligonucleotide, causing said first and second identiphores to covalently bond with each other, wherein said covalent bonding gives rise to a signal detectable by spectroscopy, wherein said signal is absent in said first and second oligonucleotides prior to said covalent bonding; and identifying said cells by spectroscopic detection of said signal.

2. The method of claim 1 wherein said oligonucleotides orient said identiphores into spatial proximity when bound to said nucleic acid.

3. The method of claim 1 wherein said oligonucleotides orient said identiphores into a preselected geometric configuration when bound to said nucleic acid.

4. The method of claim 1 wherein said detection comprises X-ray, magnetic resonance, proton magnetic resonance, electron spin resonance, fluorescence, or electromagnetic spectroscopy.

5. The method of claim 1 wherein the presence of said preselected nucleic acid sequence is diagnostic for a cellular biological state.

6. The method of claim 5 wherein said cellular biological state is a disease state.

7. The method of claim 5 wherein said cellular biological state is a hyperproliferative state.

8. The method of claim 5 wherein said cellular biological state is a cancerous state.

9. The method of claim 1 wherein said identiphores form a new molecular species upon coming into proximity with each other.

* * * * *